United States Patent [19]
Vandre

[11] Patent Number: 5,919,129
[45] Date of Patent: Jul. 6, 1999

[54] FIBER OPTIC PERIODONTAL ENDOSCOPE

[75] Inventor: Robert H. Vandre, Middletown, Md.

[73] Assignee: The United States of America as represented by the Secretary of the Army, Washington, D.C.

[21] Appl. No.: 08/775,427

[22] Filed: Jan. 9, 1997

[51] Int. Cl.$^6$ ..................................................... A61B 1/00
[52] U.S. Cl. ......................... 600/170; 600/160; 600/182; 433/29; 433/72
[58] Field of Search ..................................... 600/160, 170, 600/171, 176, 177, 178, 179, 182, 137, 136; 433/29, 72

[56] References Cited

U.S. PATENT DOCUMENTS

| | | | |
|---|---|---|---|
| 5,051,823 | 9/1991 | Cooper et al. | 433/29 |
| 5,328,365 | 7/1994 | Jacoby | 433/29 |
| 5,743,731 | 4/1998 | Lares et al. | 433/29 |

*Primary Examiner*—Beverly M. Flanagan
*Attorney, Agent, or Firm*—Charles H. Harris; John Francis Moran

[57] ABSTRACT

A fiber optic periodontal endoscope includes a lens and light housing assembly attached to a handle end tip containing fiber optic bundles transmitting light from the source to illuminate the probe tip. The returning image traveling back through the handle along the fiber optic bundle is reflected off a mirror toward the magnification lens housed in a portion of the assembly which is at right angles to the light housing portion. The probe has two rotating joints, one between the tip and handle and the other between the assembly and handle to enable rotation of the lens for ease of viewing and additional rotation of the probe tip to allow for illumination and visualization at the side of the tip.

19 Claims, 7 Drawing Sheets

FIBER OPTIC PERIODONTAL ENDOSCOPE

TECHNICAL FIELD

The present invention relates generally to endoscope devices and, more particularly, to a fiber optic periodontal endoscope instrument.

BACKGROUND ART

Presently the only way a dentist can see a tooth surface below the level of the gingiva is to anesthetize the patent and surgically expose the area. Normally the dentist does not choose to surgically expose a subgingival area. Instead, he tries to find calculus and foreign objects on tooth surfaces by feeling the surface with a sharp explorer instrument.

Periodontal probes for measuring the depths of pockets or recesses which form between the tooth and the gum and for use in endodontic techniques involving measurements of root canals are known. A periodontal endoscope called the Perioscope has been reported in the literature. This device utilizes a 1.2 mm diameter coherent fiber optic endoscope with a wide angle lens at its tip. Also attached to the tip is a 5 mm long guide plate which is used to retract the anesthetized gingiva of the patient being examined. The image in the Perioscope is viewed by the dentist by putting his eye to the lens at the other end of the Perioscope. The Perioscope allows visualization of both the root and the epithelial wall of the pocket at a 4× magnification. The device is described in the following journal article:

Matsumoto K., Nakano K., Kojima T.: Direct Observation of the Root Wall and Pocket Tissue, Quintessence Int. 19:483, 1988.

However, the foregoing Perioscope can be difficult to use due to an inability to adjust the position of the lens relative to the Perioscope body as well as the light beam emanating from the fiber optic probe tip. Another difficulty with the Perioscope is that the gingiva must be anesthetized and reflected before the root can be fully visualized.

SUMMARY OF THE INVENTION

It is accordingly an object of the present invention to enable a dentist to see a tooth surface below the level of the gingiva without anesthetizing the patent and surgically exposing the area.

Another object of the invention is to enable the dentist to locate calculus and foreign objects on tooth surfaces without the use of sharp explorers.

Still another object of the present invention is to provide a fiber optic periodontal probe wherein the imaging lens and point of illumination emanating the probe are each easily and individually adjustable.

An additional object of the invention is to provide direct linear measurement of gaps in restoration margins and to find cracks in root surfaces.

Still another object is to provide a fiber optic probe having easily detachable fiber optic probe tips of varying cross-section to optimize the illuminated viewing area in relation to the size and topology of the surface over which the probe travels.

A fiber optic periodontal endoscope, in accordance with the present invention, comprises an assembly containing an image magnifying viewer and a light source. A handle containing a coherent fiber optic image conduit is connected to the assembly to transmit light from the light source to the surface of the tooth and to transmit the image of the tooth surface back to the assembly means. A tip containing a coherent fiber optic image conduit is connected to the handle for transmitting light and the image to and from the tooth surface.

The assembly may also include a mirror for reflecting the image from the coherent fiber optic image conduit in the handle up through a magnifier housing of the assembly. The magnifying viewer housing has an optical viewing axis which is at right angles to the optical axis of the image conduit in the handle.

The tip is preferably rotatably secured to the front end of the handle to permit rotation of the forwardmost end of the fiber optics in the tip about the longitudinal axis of the tip. The handle is also preferably rotatably secured to the assembly means to permit rotation of the magnifier about the longitudinal axis of the handle. In this manner, the positioning of the viewer is adjustable independent of the point of illumination of the tip.

The fiber optic bundle in the handle is preferably self-contained and therefore has opposite ends terminating at opposite ends of the handle and polished to an optical surface. Likewise, the fiber optics in the tip are preferably self contained therein with opposite ends terminating proximate opposite ends of the tip.

The rear end of the handle is received within a bore located in the front end of the assembly means. An annular boss of greater diameter than the rear end of the handle is seated against the front end of the assembly means and captured by a first threaded cap for rotatable mounting against the front end. The handle extends forwardly from the cap through a central opening in the cap end wall.

The front end of the handle is preferably bent at right angles to the handle longitudinal axis. The imager tip therefore extends at right angles to the handle longitudinal axis. The fiber optic bundle defining the forwardmost end of the imager tip is preferably bent through an additional 90° and optically finished to define a probe tip residing in a plane parallel to the longitudinal axis of the imager tip and perpendicular to the longitudinal axis of the handle.

The imager tip is formed with a collet having a tubular portion terminating in a rear annular boss rotatably mounted to the front end of the handle with a second threaded cap. The fiber optics in the imager tip extend through the collet with the rear end of the fiber optics being flush and mirror finished with respect to the rear end face of the annular boss. In this manner, the fiber optics in the handle and tip abut each other to permit reliable optical transmission of the image. If desired, an immersion oil may be disposed at the fiber optic interface between the handle and tip to minimize image degrading reflections.

Still other objects and advantages of the present invention will become readily apparent to those skilled in this art from the following detailed description, wherein only the preferred embodiments of the invention are shown and described, simply by way of illustration of the best mode contemplated of carrying out the invention. As will be realized, the invention is capable of other and different embodiments, and its several details are capable of modifications in various obvious respects, all without departing from the invention. Accordingly, the drawing and description are to be regarded as illustrative in nature, and not as restrictive.

DETAILED DESCRIPTION

Figure 1:
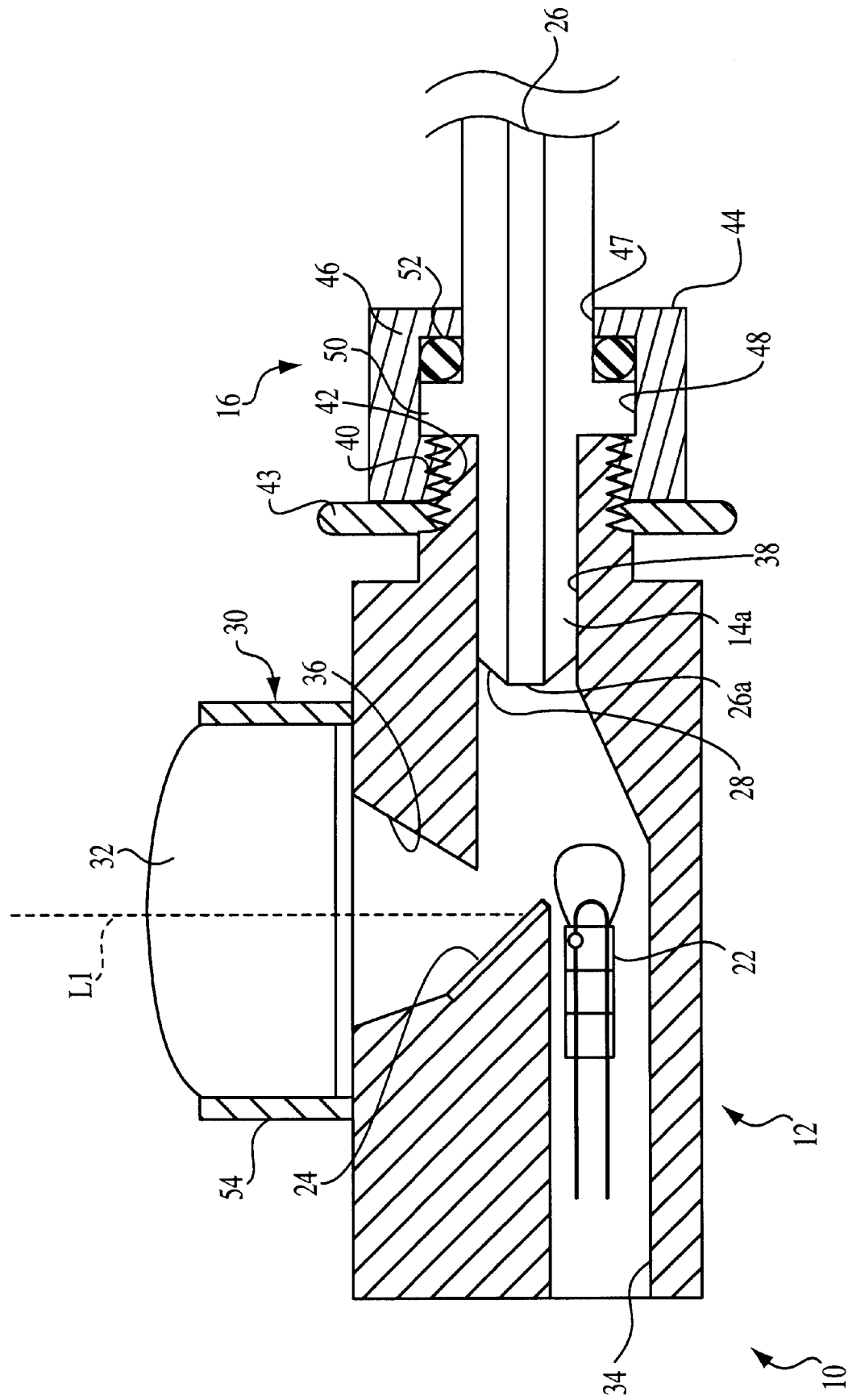
FIG. 1 is a sectional view of a light and magnifying viewer assembly of the fiber optic periodontal probe of the present invention.

A fiber optic periodontal endoscope 10, in accordance with the invention, is of three-part construction comprising a viewer and light assembly 12 (FIG. 1), a handle 14 (FIG. 2) attached to the assembly with a rotary joint 16, and a fiber optic tip 18 (FIGS. 3–6) attached to the front end of the handle with a rotary joint 20.

In FIG. 1, light is transmitted from a bulb 22 through a coherent fiber optic bundle 26 (e.g., 1.5 mm diameter) that makes a right angle bend at tip 25 (see FIG. 3) in the forward end of handle 14. The fiber optic bundle 26 is preferably optically mirror finished and terminates flush with opposite ends of handle 14. Light transmitted through fiber optic bundle 26 at the handle forward end 25 enters a second coherent fiber optic bundle 27 in probe tip 18. At the distal end 18a of the probe tip 18, the fiber optic bundle 27 makes another right angle bend so that the light travels out the side of the probe tip 18 rather than straight out the distal end. This allows illumination and visualization at the side of the tip 18a where it is most needed. The light then reflects off of the object being viewed creating an image which travels back along the fiber optic bundles 27,26. When the image reaches the magnifying viewer and light assembly, it is reflected by a front surface mirror upwardly through a lens holder 30 into, for example, a 23 mm focal length achromatic lens 32 providing approximately 4× magnification.

The viewer and light assembly 12, as depicted in FIG. 1, is formed from cylindrical rod stock having a rear cavity 34 open at the rear end thereof for receiving a light bulb 22 (e.g., 3 volt miniature flashlight bulb). Placed above this cavity is a front surface mirror 24 placed at a 45 degree angle from the long axis of the rod. The mirror is placed such that it keeps light from the light bulb from traveling directly up into the optics of the magnifier but still allows the image exiting the coherent image conduit in the handle to be viewed by the magnifying optics. The front end of the rod stock has a cylindrical cavity 38 which intersects the light bulb's cavity and the front surface of the mirror. Intersecting the intersection of these two cavities is a third cavity 36 which extends laterally from the front surface of the mirror opening to the side wall of the cylindrical stock. The rear end 26a of the fiber optic bundle 26 terminates flush with the rear end 14a of the handle 14 which is received within a longitudinally extending cylindrical passage 38 formed in a front end portion of the cylindrical stock extending forwardly of the beam splitter 24.

In FIG. 1, the forwardmost end of the stock is formed with a plurality of threads 40 cooperating with like threads 42 in the rotary joint 16. More specifically, the rotary joint 16 is in the form of a cylindrical cap 44 having a front end wall 46 with a central opening 47 through which the handle 14 extends and a rearwardly directed cylindrical cavity 48 of which the front end wall defines the bottom thereof. The cylindrical cavity inner side wall is formed with the threads 42 at its rearmost end while the bottom of the interior cylindrical side wall is of uniform diameter to receive an annular boss 50 of the handle (of greater diameter than the handle and corresponding to the diameter of the interior side wall). An O-ring 52 is captured between the boss 50 and front end wall 46 to give uniform resistance to rotations of the joint. A lock nut 43 keeps the cylindrical cap 44 from rotating when the joint is rotated.

In FIG. 1, extending laterally from the light assembly is magnifying viewer assembly 30 in the form of a cylindrical tube 54 having a central longitudinal axis L1 intersecting the reflection surface 24a of the mirror 24. The magnifier tube 54 contains lens 32 in its outer end which is adapted to receive the image reflected from the object being scanned.

Figure 2:
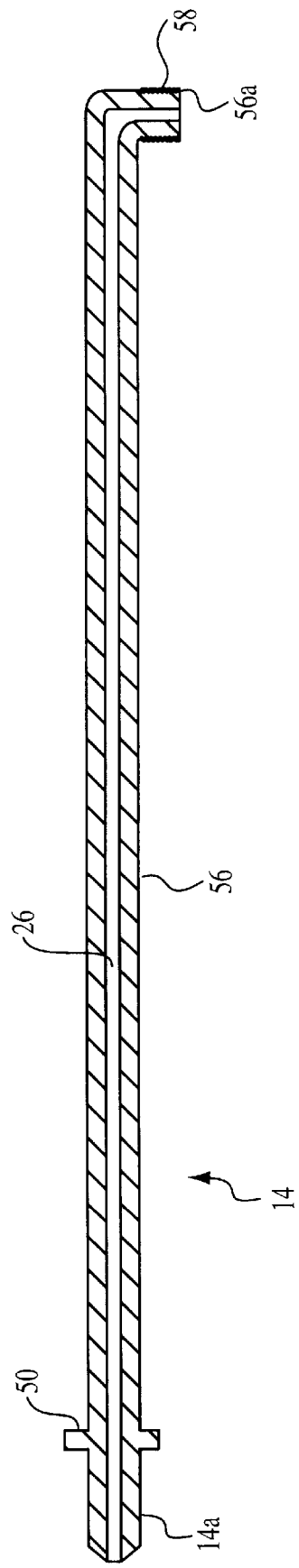
FIG. 2 is a sectional view of the handle of the probe.
Figure 3:
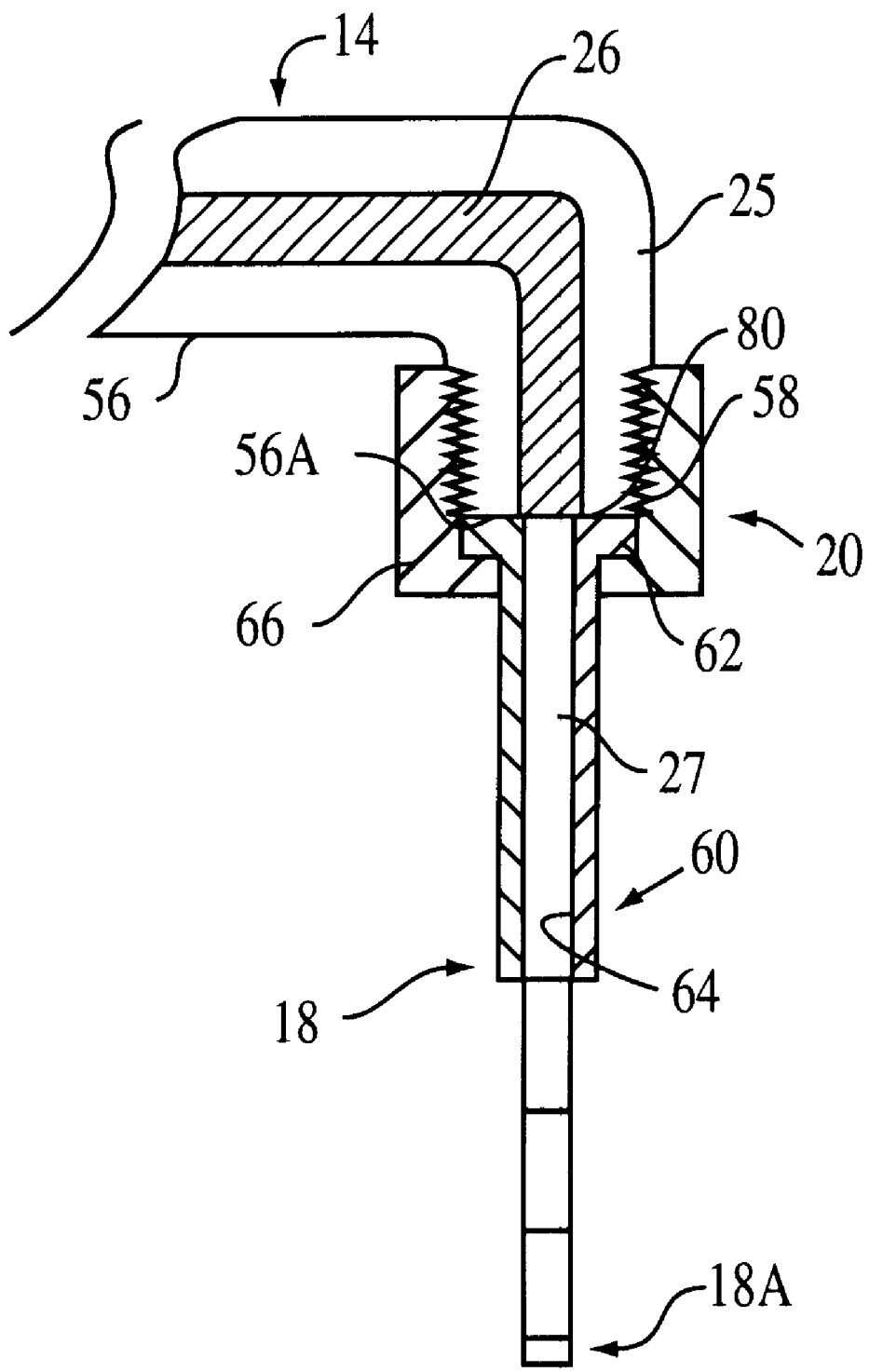
FIG. 3 is an enlarged sectional view of the probe tip attached to the handle.

Handle 14, as best depicted in FIG. 2, is an elongate member having a cylindrical surface 56 with annular boss 50 for rotatably securing the rear end of the handle to the assembly via rotary joint 16 in the manner described above. With reference to FIGS. 2 and 3, the front end of handle 14 is at right angles to the handle body and is formed with an exterior thread 58 for rotatably securing the imager tip 18 to the front end with rotary joint 20 in the manner described more fully below. The coherent fiber optic bundle 26 extends from a rear position flush with the rear end of the handle 14 through a central passageway formed in the handle and terminates flush with the front end 56a thereof. Both ends of the bundle 26 are orthogonal to the long axis of the bundle and polished to an optical finish. The rear end of the handle is beveled 28 at a 45 degree angle with the long axis of the handle to minimize light reflection from the rear end of the handle.

Figure 4:
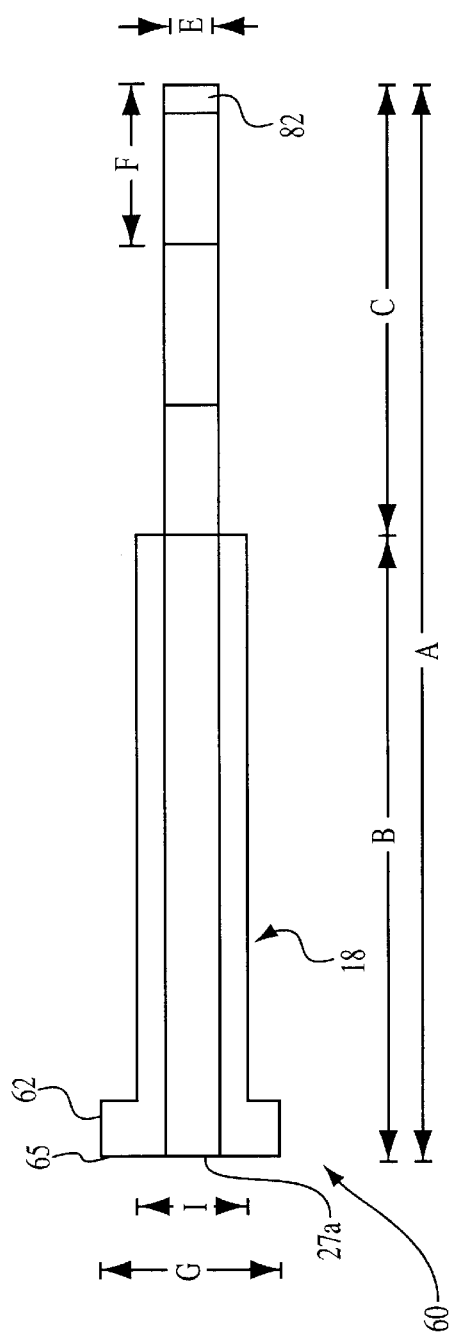
FIGS. 4 and 4A are bottom and side sectional views of one embodiment of a probe tip.
Figure 4A:
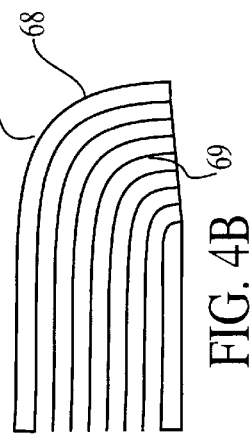
Figure 5:
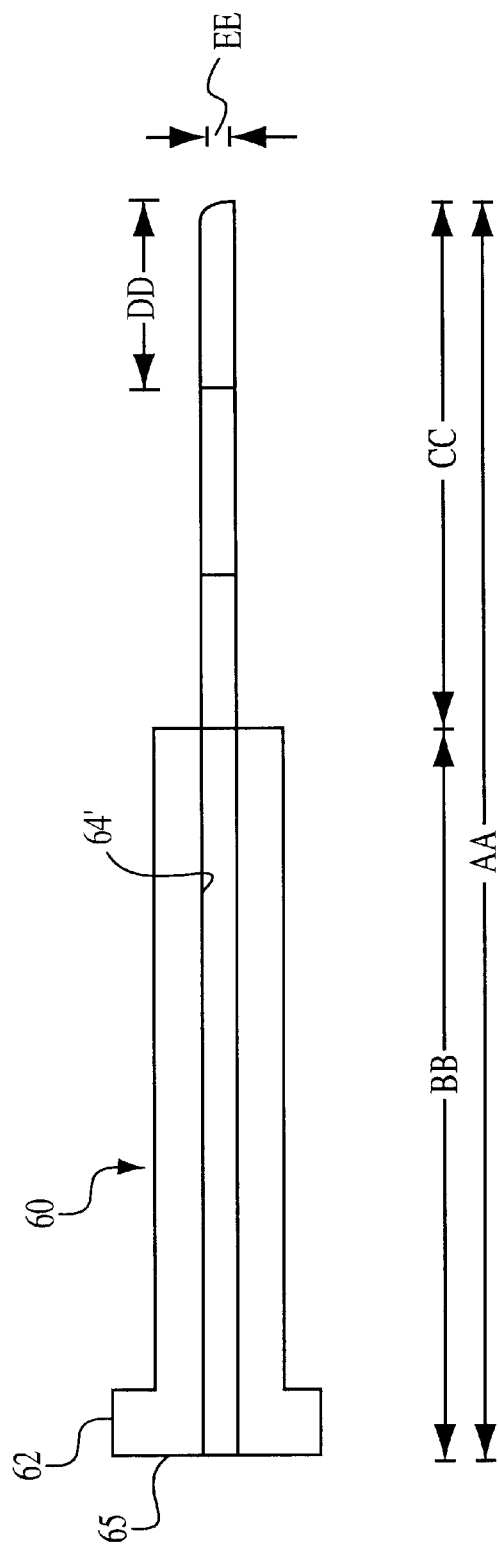
FIGS. 5 and 5A are side and bottom sectional views of a second embodiment of a probe tip of the invention.

FIG. 3 is an illustration of an imager tip 18 with specific embodiments thereof depicted in FIGS. 4, 4A, 5, 5A, 5B, and 6. Common to each embodiment is a collet 60 in the form of a cylindrical sleeve (of stainless steel or plastic) having an annular boss 62 at the rear end thereof. A central longitudinal passageway 64 extends through the collet 60 and boss 62 to receive the fiber optic bundle 27 extending through the collet and terminating in a fiber optic tip 18a as depicted in FIGS. 4 and 5. The rotary joint 20 is defined by an internally threaded end cap 66 corresponding to the construction of cap 44 to rotatably secure the imager tip 18 to the front end 56a of the handle 14.

Figure 4B:
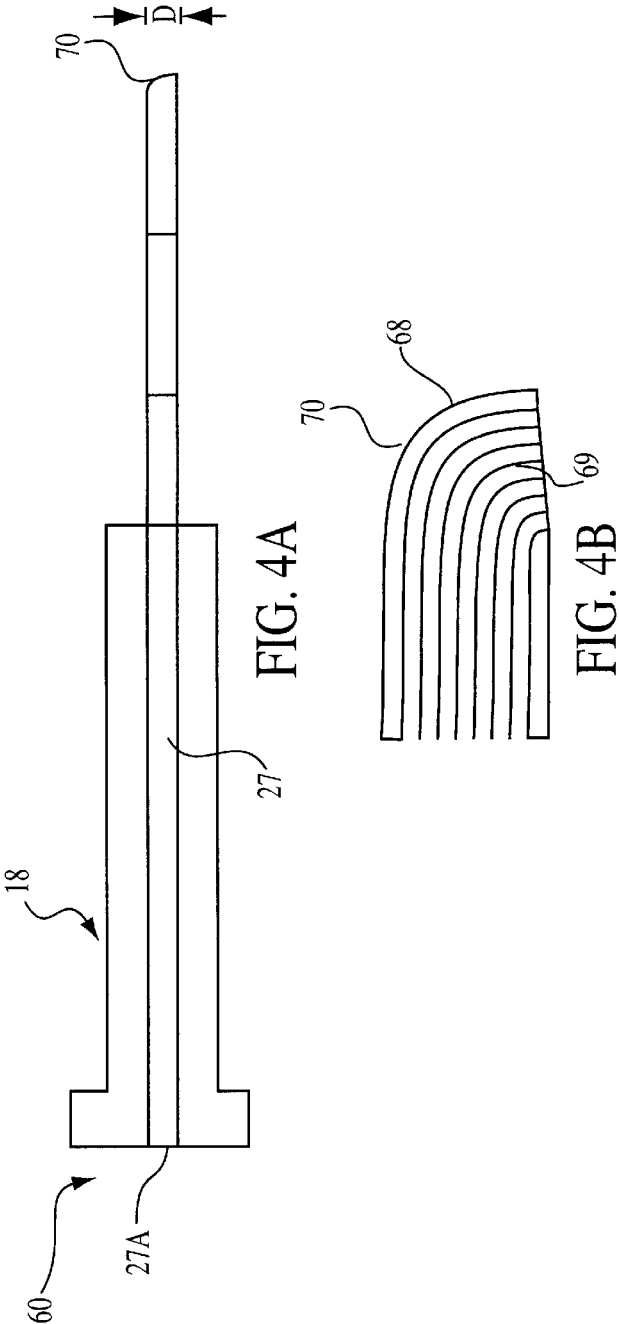

FIGS. 4, 4A, and 4B are illustrations of a rectangular probe tip which is essentially a coherent fiber optic bundle of rectangular cross-section (e.g., 1.0×0.5 mm) extending through the central longitudinal passageway of the collet of the imager tip 60 of like cross-section. The rear end 27a of this fiber optic bundle 27 is optically finished and flush with the base 65 of the collet 60 defined by the rear facing surface of the annular boss 62. The fiber optic bundle 27 may be coated with a thin plastic coating 68 which holds the glass fibers 69 together in case they are broken. The forwardmost end of the fiber optic bundle 27 makes a right angle bend at 70 and is cut off flush with the side of the bundle. The final 9 mm of the probe tip may be coated alternating black and white at 3 mm intervals for use by the dentist as a depth reference.

The following dimensional characteristics may be used in conjunction with the imager tip of FIG. 4:

Dimension A=20 mm
Dimension B=14 mm
Dimension C=6 mm
Dimension D=0.5 mm
Dimension E=1.0 mm Dimension F=3.0 mm Dimension G=0.130 in.

Dimension H=0.080 in.

Dimension I=0.040 in.

Figure 5A:
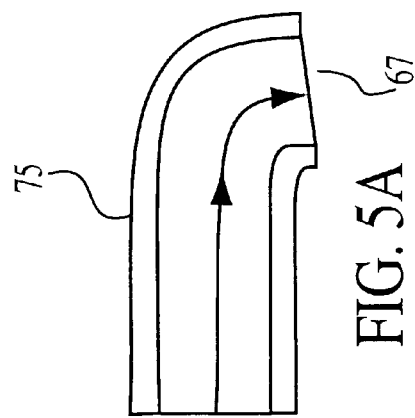

FIGS. 5 and 5A are illustrations of a second embodiment of an imager tip wherein the collet of FIG. 4 is used to contain a round fiber optic probe tip 67 defined by a coherent fiber optic bundle of cylindrical cross-section (FIG. 5A) extending through a central longitudinal passageway 64' of the collet of like cross-section and terminating at its forwardmost end in a right angle bend at the tip which is cut off flush with the side of the bundle to define the round tip 67. This fiber optic bundle may be placed inside a thin walled hypodermic needle tubing 75 (e.g., 22 gauge, thin wall and 0.7 mm outer diameter to allow a 0.5 mm fiber optic bundle to be placed inside). The feature of using needle tubing 75 makes this probe tip much more rugged and also allows better control of the glass fragments should the fiber optic glass shatter.

The following dimensional relationships apply with respect to the FIG. 5 probe tip:

Dimension AA=20 mm

Dimension BB=11 mm

Dimension CC=9 mm

Dimension DD=3.0 mm

Dimension EE=0.5 mm

Figure 6:
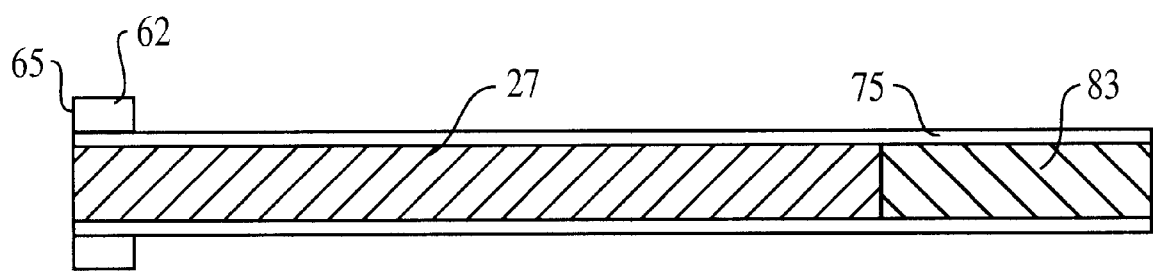
FIG. 6 is a side sectional view of a third embodiment of a probe tip.

FIG. 6 is an illustration of a third embodiment of an imager tip. In this tip, stainless steel tubing 75 (e.g., 5/64 inch, 0.012 inch wall) has an annular boss equivalent to the one in FIG. 4 brazed to the end of the tubing effectively making the entire tube a collet. A coherent fiber optic imaging bundle 27 fills the rear portion of the tube. A self-focusing rod lens (e.g., Nippon Sheet Glass SELFOC imaging lens) forms a butt joint with the end of the imaging bundle and is epoxied to the bundle with optical epoxy. The lens acts as a wide angle lens with a 5 mm focal length. This probe can be used to view the interior of extraction sockets or other areas that are commonly hidden from view in the oral environment.

Figure 7:
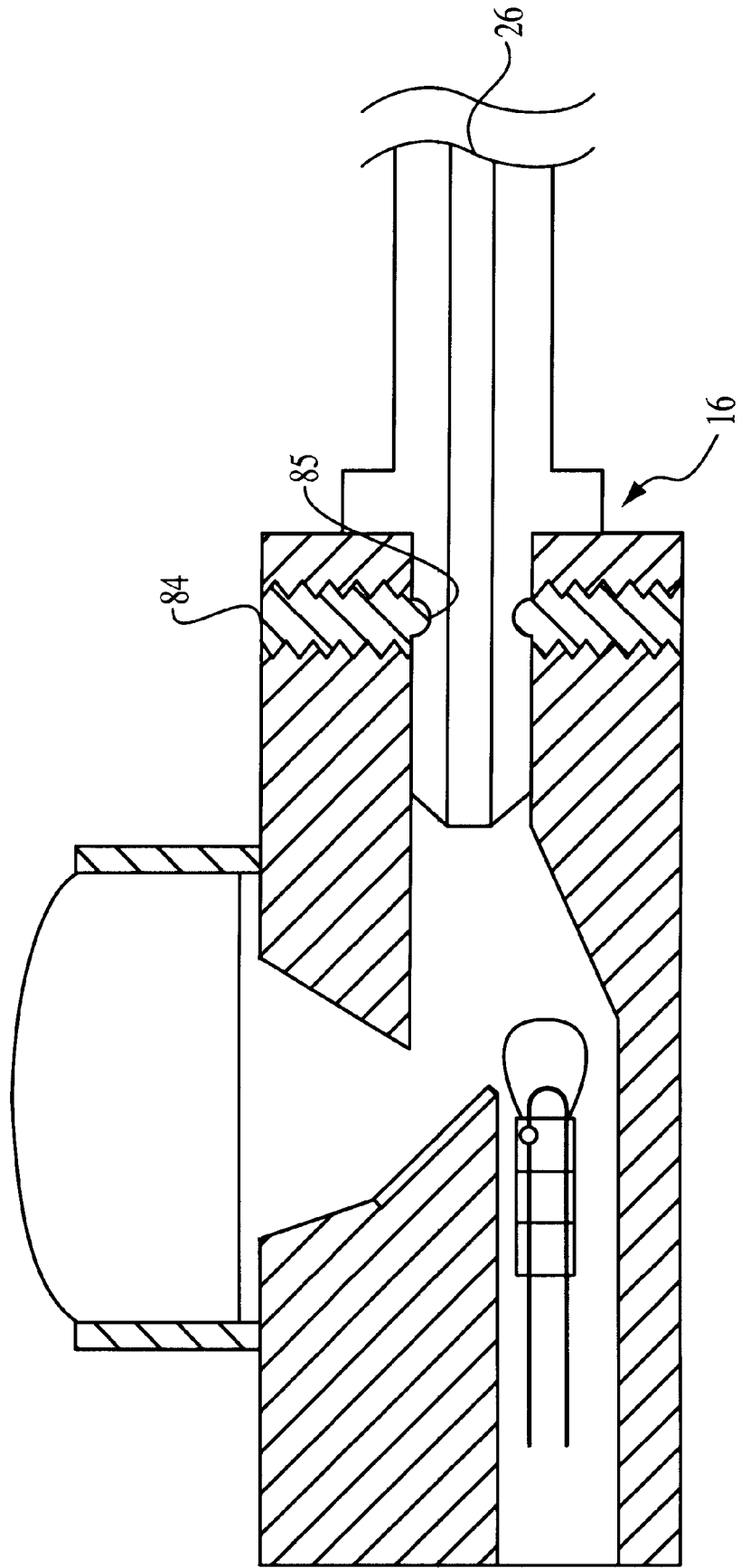
FIG. 7 is a sectional view of a second embodiment of the light and magnifying viewer assembly depicted in FIG. 1.

FIG. 7 is an illustration of a second embodiment of the rotary joint shown in FIG. 1. In this embodiment the handle is retained by two ball plungers 84. The balls of which snap into a detent groove 85 placed on the shaft of the handle. This allows easier assembly and disassembly of the endoscope, simplifies manufacturing, and acts as a stress breaker if the endoscope is dropped.

The primary advantage of the fiber optic periodontal probe 10 of this invention is that it enables a dentist to visualize the surfaces of a crown, root and sulcus at a predetermined magnification (e.g., 4x) without the need for anesthesia or reflecting a flap. The ability to view the inner surface of the periodontal sulcus may prove helpful in diagnosis of incipient soft tissue pathology. Other possible uses would be to directly examine crown margins and to make sure crown margins are below existing restorations. The device may prove useful in visualizing vertical fractures of the crown and root. It may also be possible to directly view the interproximal surfaces of the teeth directly below their contact points and look for interproximal decay.

By placing a small bend in the currently designed end-looking probe tip of FIG. 6, a curved end-looking probe tip could be produced. This probe tip could prove valuable in periodontal surgeries to view areas of the root surface which are impossible to see otherwise, such as beneath the furcation. In another modification, the use of a smaller diameter rod lens would allow fabrication of a probe tip capable of being introduced into root canals. Various such modifications are believed obvious to one of ordinary skill from reviewing this disclosure.

The rotating joint 16 between the viewer and light assembly 12 and the handle 14, allows the active area of the probe tip 18a to be rotated in any direction about the longitudinal axis L of the handle to enable the operator to swivel the lens 32 around so that he can position the lens for ease of viewing. The lens 32 is focused so that the operator can see the image at a distance of 0–100 cm from the magnifying lens. Adding different lens combinations can increase magnification, as desired by the operator.

The front rotary joint 20 between the imager tip 18 and handle 14 allows the active area of the probe tip to be rotated in any direction about the longitudinal axis of the collet 60 so that the operator can visualize any surface of the tooth or sulcus.

Immersion oil 80 may be used to minimize image degrading reflections at each fiber optic interface.

The rectangular fiber optic tip 82 of FIG. 4 allows the operator to view a 1x0.5 mm area of the tooth or sulcus surface. The round probe tip of FIG. 5 allows the operator to view a 0.5 mm area on the tooth surface. Both of these views are a small area of the tooth surface and if placed in only one spot would probably provide very little information to the operator. However, the real information is gained as the operator moves the probe around the tooth's surface and watches the surface through the probe during such movement.

It will be readily apparent to one of ordinary skill in the art that the present invention fulfills all of the objects set forth above. After reading the foregoing specification, those skilled in the art will be able to effect various modifications, changes, substitutions of equivalents and various other aspects of the invention as broadly disclosed herein. It is therefore intended that the protection granted hereon be limited only by the scope of the invention as set forth in the appended claims and equivalents thereof.

I claim:

1. A fiber optic periodontal endoscope, comprising:
   (a) assembly means for containing a light source and a viewer;
   (b) handle means containing a fiber optic bundle and connected to the assembly means for transmitting light from the light source in a first direction through said fiber optic bundle and an image back through the fiber optic bundle in a second direction opposite the first direction;
   (c) tip means containing fiber optics and connected to the handle means for transmitting light to illuminate an object and for receiving the image reflected from the object;
   means for rotatably securing the handle means to the assembly means to permit rotation of the viewer about the longitudinal axis of the handle means;
   means for rotatably securing the tip means to the handle means to enable rotation of a forwardmost end of the fiber optics in the tip means about the longitudinal axis of the tip means independent of rotation of the handle means relative to the assembly means.

2. The endoscope of claim 1, wherein a forwardmost end of the fiber optics in the tip means is rectangular in plan view and resides in a plan extending generally parallel to the longitudinal axis of the tip means.

3. The endoscope of claim 1, wherein a forwardmost end of the fiber optics in the tip means is circular in plan view and resides in a plan extending generally parallel to the longitudinal axis of the tip means.

4. The endoscope of claim 1, wherein said assembly means includes viewer tubular housing means extending laterally from the assembly means for housing the viewer in operative alignment with the light source and fiber optic bundle within the handle means.

5. The endoscope of claim 1, wherein said handle means is formed with an annular boss at a rear end thereof of larger diameter than forward and rearward portions of the handle means extending adjacent thereto, the rearwardly extending portion being received within a front end portion of the assembly means with the annular boss seated against the front end, and cap means rotatably mounted to the front end to permit rotation of the handle means relative to the assembly means.

6. The endoscope of claim 5, wherein said cap means includes a cylindrical side wall connected to an end wall defining with the side wall a cylindrical cavity opening to the rear of the cap means, the end wall including a circular opening through which the handle means extends from the boss captured in the bottom portion of the recess, an interior cylindrical side wall portion of the recess extending forwardly of the boss being threaded to enable threaded engagement with a corresponding thread formed on the forward end portion of the assembly means, and sealing means disposed between the boss and bottom of the recess.

7. The endoscope of claim 1 or 5, wherein the fiber optic bundle extends axially in the handle means forming a coherent bundle terminating at opposite ends of the handle means.

8. The endoscope of claim 7, wherein said opposite ends of the coherent bundle are polished to an optical surface.

9. The endoscope of claim 7, wherein said tip means includes a collet of hollow tubular construction formed with a boss at a rear end thereof of larger diameter than the tubular member.

10. The endoscope of claim 9, wherein said boss is received against a front end face of the handle means and second cap means capturing the boss and rotatably mounted to the front end of the handle means to enable rotation of the tip means relative to the handle means.

11. The endoscope of claim 10, wherein the fiber optics in the tip means is a coherent bundle terminating at opposite ends of the tip means.

12. The endoscope of claim 11, wherein said opposite ends are polished to define optic surfaces at the ends of the top means.

13. The endoscope of claim 1, wherein a forwardmost end of the handle means is angled relative to the longitudinal axis of the handle means.

14. The endoscope of claim 13, wherein the forwardmost end of the fiber optics in the tip means is bent through approximately a 90° angle relative to the longitudinal axis of the tip means.

15. The endoscope of claim 11, wherein the fiber optic bundle in the tip means is of rectangular cross section and covered with a thin plastic reinforcement coating.

16. The endoscope of claim 11, wherein the fiber optic bundle in the tip means is of circular cross section received within a tubing contained within the tip means.

17. The endoscope of claim 11, wherein a forwardmost end of the fiber optics in the tip means includes a coated surface defining, for the operator, a visual reference marker to facilitate location of the forwardmost end.

18. A fiber optic periodontal endoscope, comprising:
   (a) assembly means for containing a light source and a viewer;
   (b) handle means containing a fiber optic bundle and connected to the assembly means for transmitting light from the light source through the fiber optic bundle and the reflected image back to the viewer;
   (c) tip means containing fiber optics and connected to the handle means for transmitting light to illuminate an object and the image reflected from that object;
   (d) mirror means within the assembly means for directing the image from the fiber optic bundle of the handle at right angles into the viewer; and
   (e) the light source being placed off axis and within the cone of acceptance of the fiber optic bundle in the handle means to introduce light into the bundle, and the bulb being placed behind the mirror means to shield it from direct view by the viewer.

19. A fiber optic periodontal endoscope comprising:
   a first assembly including a light source and a viewer;
   a fiber optic bundle configured to transmit light from said light source to said viewer;
   a handle surrounding at least a portion of said fiber optic bundle and connected to said first assembly, said handle configured to transmit light from said light source in a first direction through said fiber optic bundle and an image back through said fiber optic bundle in a second direction opposite the first direction;
   a tip assembly surrounding at least a portion of said fiber optic bundle and connected to said handle, said tip assembly configured to transmit light for illuminating an object and for receiving an image reflected from the object.

* * * * *